(12) United States Patent
Pautsch et al.

(10) Patent No.: US 11,510,629 B2
(45) Date of Patent: Nov. 29, 2022

(54) SYSTEMS AND METHODS FOR DETECTING PATIENT STATE IN A MEDICAL IMAGING SESSION

(71) Applicant: General Electric Company, Schenectady, NY (US)

(72) Inventors: Adam Gregory Pautsch, Oconomowoc, WI (US); Robert Senzig, Waukesha, WI (US); Christopher Unger, Waukesha, WI (US); Erik Kemper, Franklin, WI (US)

(73) Assignee: General Electric Company, Schenectady, NY (US)

( * ) Notice: Subject to any disclaimer, the term of this patent is extended or adjusted under 35 U.S.C. 154(b) by 835 days.

(21) Appl. No.: 16/232,708

(22) Filed: Dec. 26, 2018

(65) Prior Publication Data

US 2020/0205748 A1 Jul. 2, 2020

(51) Int. Cl.
| | |
|---|---|
| *A61B 5/00* | (2006.01) |
| *A61B 5/055* | (2006.01) |
| *A61B 5/11* | (2006.01) |
| *A61B 5/16* | (2006.01) |
| *A61B 6/03* | (2006.01) |
| *A61B 6/00* | (2006.01) |
| *A61B 8/08* | (2006.01) |

(52) U.S. Cl.
CPC .......... *A61B 5/7289* (2013.01); *A61B 5/0077* (2013.01); *A61B 5/055* (2013.01); *A61B 5/1114* (2013.01); *A61B 5/1128* (2013.01); *A61B 5/165* (2013.01); *A61B 5/4812* (2013.01); *A61B 5/7292* (2013.01); *A61B 5/7455* (2013.01); *A61B 6/032* (2013.01); *A61B 6/037* (2013.01); *A61B 6/485* (2013.01); *A61B 8/5276* (2013.01)

(58) Field of Classification Search
CPC combination set(s) only.
See application file for complete search history.

(56) References Cited

U.S. PATENT DOCUMENTS

| | | | |
|---|---|---|---|
| 2005/0201510 A1 | 9/2005 | Mostafavi | |
| 2009/0003655 A1* | 1/2009 | Wollenweber | ........ G06T 11/005 382/107 |

(Continued)

FOREIGN PATENT DOCUMENTS

| | | |
|---|---|---|
| JP | 2008206740 A | 9/2008 |
| WO | 2016030537 A1 | 3/2016 |

OTHER PUBLICATIONS

European application No. 19219561.8 filed Dec. 23, 2019—Extended Search Report dated Jul. 15, 2020; 12 pages.

(Continued)

*Primary Examiner* — Joel F Brutus
(74) *Attorney, Agent, or Firm* — McCoy Russell LLP (57) ABSTRACT

Methods and systems are provided for detecting patient motion during a diagnostic scan. In one example, a method for a medical imaging system includes obtaining output from one or more patient monitoring devices configured to monitor a patient before and during a diagnostic scan executed with the medical imaging system, receiving a request to initiate the diagnostic scan, tracking patient motion based on the output from the one or more patient monitoring devices, and initiating the diagnostic scan responsive to patient motion being below a threshold level.

20 Claims, 7 Drawing Sheets

(56) References Cited

U.S. PATENT DOCUMENTS

| | | | |
|---|---|---|---|
| 2009/0262885 A1* | 10/2009 | Bontus | G06T 11/006 378/11 |
| 2013/0093866 A1* | 4/2013 | Ohlhues | G01C 11/04 348/65 |
| 2013/0342851 A1 | 12/2013 | Dresel | |
| 2014/0371635 A1* | 12/2014 | Shinar | A61B 5/6892 600/595 |
| 2014/0378816 A1 | 12/2014 | Oh | |
| 2016/0000383 A1 | 1/2016 | Lee | |
| 2016/0135768 A1* | 5/2016 | Wollenweber | A61B 6/0407 600/427 |
| 2018/0140270 A1 | 5/2018 | Profio et al. | |

OTHER PUBLICATIONS

JP application 2019-219574 filed Dec. 4, 2019—Office Action dated Dec. 14, 2021; Machine Translation; 5 pages.
JP2008-206740 English Abstract; Espacenet.com search Mar. 1, 2022; 1 page.

* cited by examiner

SYSTEMS AND METHODS FOR DETECTING PATIENT STATE IN A MEDICAL IMAGING SESSION

FIELD

Embodiments of the subject matter disclosed herein relate to diagnostic imaging, and more particularly, to adjusting a diagnostic imaging session using real-time patient data such as patient motion.

BACKGROUND

Imaging technologies allow images of the internal structures of a patient or object to be obtained, and in some examples without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

BRIEF DESCRIPTION

In one embodiment, a method for a medical imaging system includes obtaining output from one or more patient monitoring devices configured to monitor a patient before and during a diagnostic scan executed with the medical imaging system, receiving a request to initiate the diagnostic scan, tracking patient motion based on the output from the one or more patient monitoring devices, and initiating the diagnostic scan responsive to patient motion being below a threshold level.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of medical imaging systems. In particular, systems and methods are provided for detecting patient motion during a medical imaging session, and adjusting one or more aspects of the imaging session based on the patient motion. Certain imaging modalities, such as CT imaging and magnetic resonance imaging, may exhibit imaging artifacts due to patient motion. These imaging artifacts may degrade the image quality to the point where diagnostic information is lost, which may result in expensive and time-consuming rescans. Further, these imaging modalities typically require the patient being imaged to be positioned in an imaging bore, separated from technicians or other people administering the imaging scan. The configuration of the bore may cause anxiety in some patients, increasing patient motion. Further, the separation between the imaging bore and the people administering the imaging scan may result in a lack of detection of patient motion and/or an inability to sufficiently address the patient motion before artifacts occur.

Thus, according to embodiments disclosed herein, one or more patient monitoring devices may be located in and/or around a medical imaging system to monitor a patient during an imaging session. The one or more patient monitoring devices may include one or more image sensors that may be mounted with a view of a patient table of a diagnostic imaging system, outside and/or inside the imaging bore. Using computer vision techniques and data from the image sensors, motion in certain areas of the imaging bore/patient table be monitored. If patient motion is detected, various actions may be taken to address the patient motion. For example, active scanning/image acquisition may be paused during patient motion. In another example, data that is acquired during periods of patient motion may be tagged and/or identified. Depending on the motion severity, the location of the motion, and a diagnostic importance of the tagged data, the tagged data may be reacquired, omitted from a final image reconstruction process, or other action. In still further examples, one or more notifications may be output to an operator of the medical imaging system and/or the patient, in order to assist the patient in reducing the motion and/or alert the operator that patient motion may be occurring. The patient motion may be tracked using the image sensors as described above, and/or the patient motion may be tracked using other patient monitoring devices such as accelerometers.

The image sensors and/or other patient monitoring devices may additionally or alternatively be used to track a patient state, such as discomfort, anxiety, or other states that may cause a patient to move or otherwise disrupt a scanning session. If a patient state is detected that should be addressed during scanning, such as patient anxiety, a notification may be output to the patient to help calm the patient. The notification may be a visual and/or audio notification that may walk the patient through various calming techniques or explain the scanning process, which may help alleviate patient anxiety. Additional calming techniques may also be implemented, such as adjusting lighting, outputting soothing sounds, outputting or adjusting displayed videos or images, etc.

Figure 1:
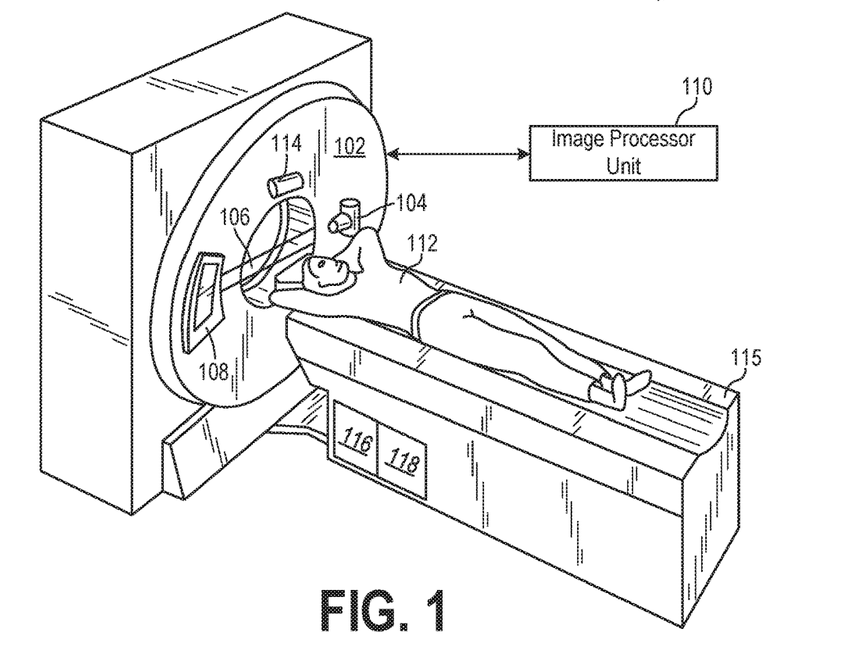
FIG. 1 shows a pictorial view of an imaging system according to an embodiment.
Figure 2:
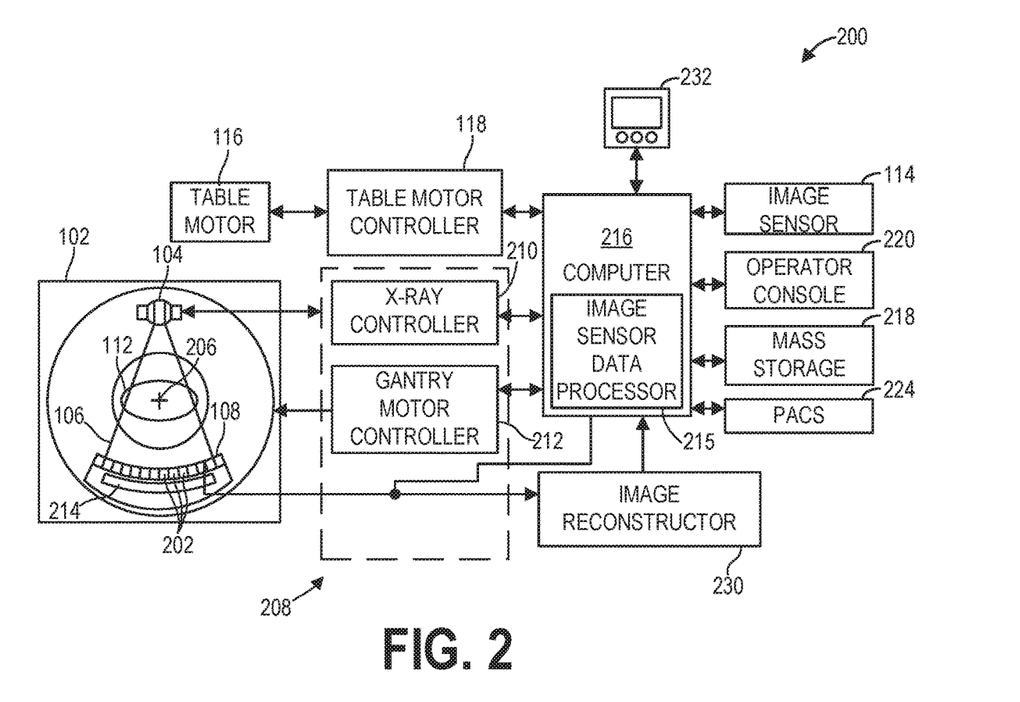
FIG. 2 shows a block schematic diagram of an exemplary imaging system according to an embodiment.
Figure 3:
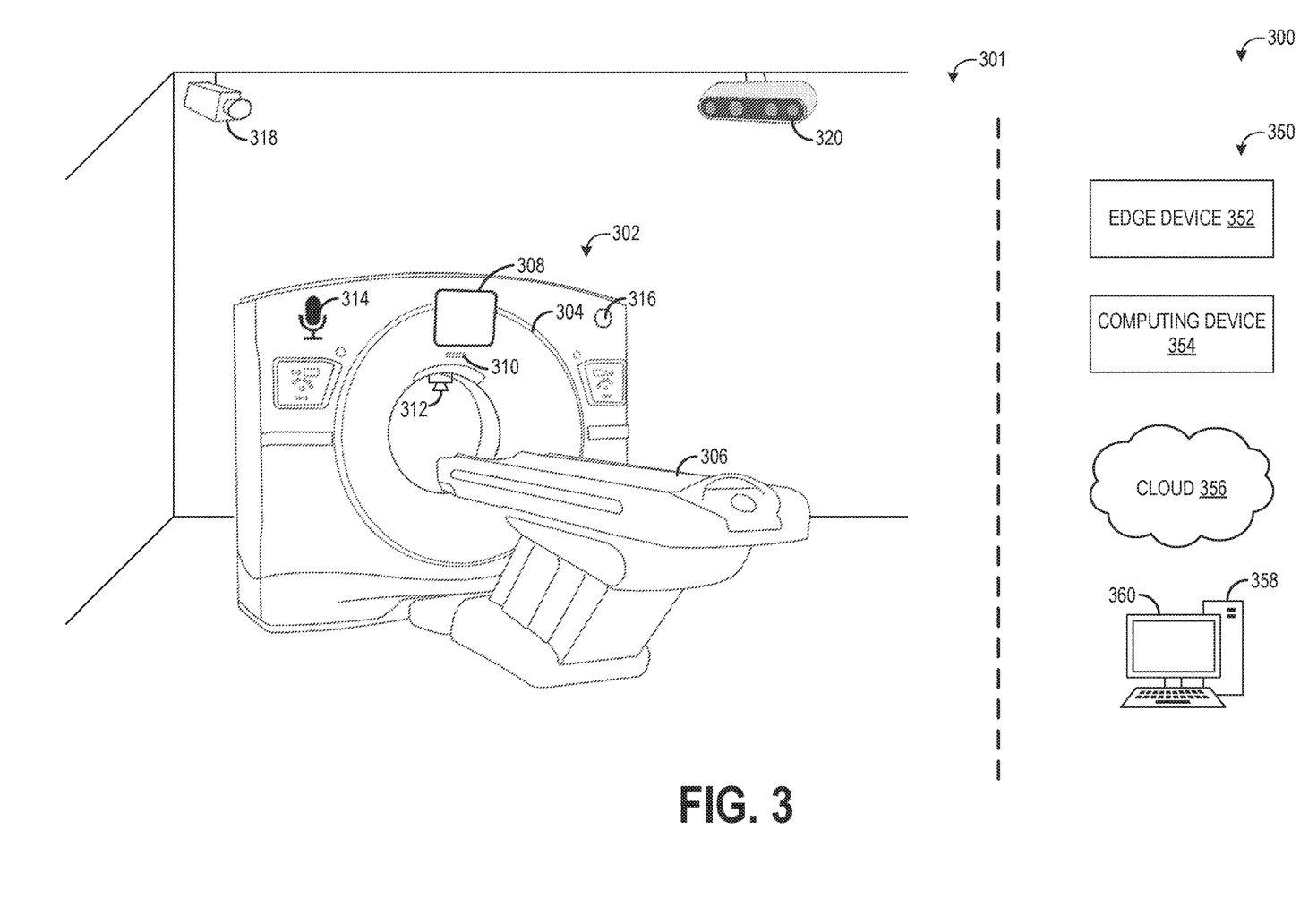
FIG. 3 shows a pictorial view of an imaging system including patient monitoring devices and interfacing hardware.
Figure 4:
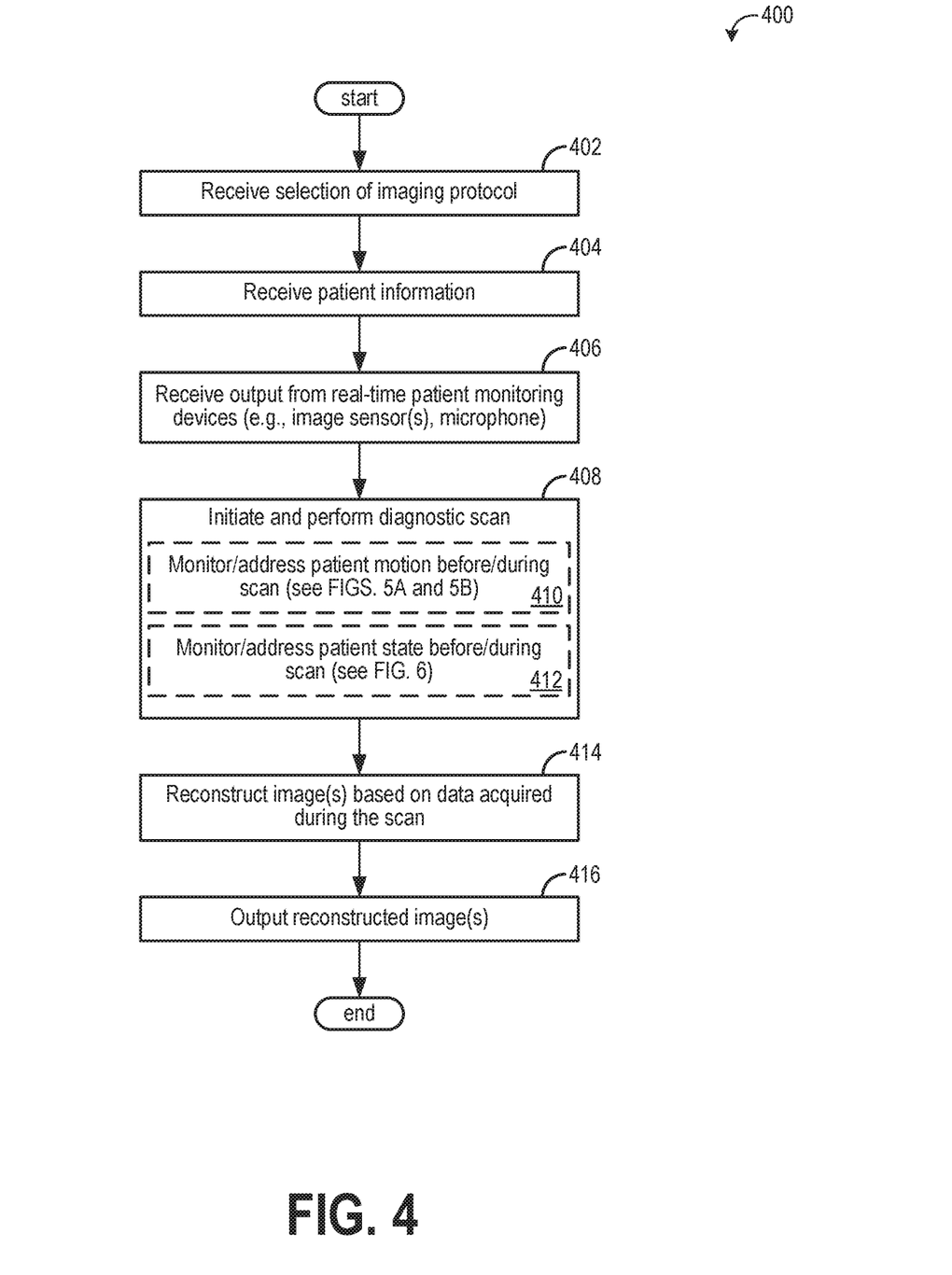
FIG. 4 is a high level flow chart illustrating a method for monitoring a patient during a medical imaging session.

An example medical imaging system in the form of a CT imaging system that may be used to acquire images and monitor a patient in accordance with the present techniques is provided in FIGS. 1-3. FIG. 4 shows a high level flow chart for monitoring a patient during an imaging session based on output from one or more patient monitoring devices of the CT imaging system. The patient monitoring may include monitoring and addressing patient movement, as described with respect to the method illustrated in FIGS. 5A and 5B, and/or monitoring and addressing a patient state, as described with respect to the method illustrated in FIG. 6. An example user interface including a notification that may be output to an operator of the CT system indicating patient movement is shown in FIG. 7, including a depiction of a skeletal model for tracking patient movement.

Though a CT system is described by way of example, it should be understood that the present techniques may also be useful when applied to imaging sessions with other imaging modalities, such as a positron emission tomography imaging system, a nuclear medicine imaging system, a magnetic resonance imaging system, an x-ray radiography imaging system, an x-ray fluoroscopy imaging system, an interventional imaging system (e.g., angiography, biopsy), an ultrasound imaging system and so forth. The present discussion of a CT imaging modality is provided merely as an example of one suitable imaging modality.

FIG. 1 illustrates an exemplary CT system 100. Particularly, the CT system 100 is configured to image a subject 112 such as a patient, an inanimate object, one or more manufactured parts, and/or foreign objects such as dental implants, stents, and/or contrast agents present within the body. Throughout the disclosure, the terms subject and patient may be used interchangeably, and it is to be understood that a patient is one type of subject that may be imaged by the CT system, and that a subject may include a patient, at least in some examples. In one embodiment, the CT system 100 includes a gantry 102, which in turn may further include at least one x-ray radiation source 104 configured to project a beam of x-ray radiation 106 for use in imaging the patient. Specifically, the radiation source 104 is configured to project the x-rays 106 toward a detector array 108 positioned on the opposite side of the gantry 102. Although FIG. 1 depicts only a single radiation source 104, in certain embodiments, multiple radiation sources may be employed to project a plurality of x-rays 106 for acquiring projection data corresponding to the patient at different energy levels.

In some examples, CT system 100 may include an imaging sensor 114 positioned on or outside the gantry 102. As shown, the imaging sensor 114 is positioned on an external side of the gantry 102 and orientated to image the subject 112 when the subject is at least partially outside the gantry 102. The imaging sensor 114 may include a visible light sensor and/or and an infrared (IR) sensor that includes an IR light source. The IR sensor may be a three-dimensional depth sensor such as a time-of-flight (TOF), stereo, or structured light depth sensor operable to generate three-dimensional depth images, while in other implementations the infrared sensor may be a two-dimensional IR sensor operable to generate two-dimensional IR images. In some implementations, a two-dimensional IR sensor may be used to infer depth from knowledge of IR reflection phenomena to estimate three-dimensional depth. Whether the IR sensor is a three-dimensional depth sensor or a two-dimensional IR sensor, the IR sensor may be configured to output a signal encoding an IR image to a suitable IR interface, which may be configured to receive the signal encoding the IR image from the IR sensor. In other examples, the imaging sensor may further include other components, such as a microphone to enable the reception and analysis of directional and/or non-directional sounds coming from an observed subject and/or other sources.

In certain embodiments, the CT system 100 further includes an image processing unit 110 configured to reconstruct images of a target volume of the patient using a suitable reconstruction method, such as an iterative or analytic image reconstruction method. For example, the image processing unit 110 may use an analytic image reconstruction approach such as filtered backprojection (FBP) to reconstruct images of a target volume of the patient. As another example, the image processing unit 110 may use an iterative image reconstruction approach such as adaptive statistical iterative reconstruction (ASIR), conjugate gradient (CG), maximum likelihood expectation maximization (MLEM), model-based iterative reconstruction (MBIR), and so on to reconstruct images of a target volume of the patient.

CT system 100 further includes a table 115 on which a subject to be imaged may be positioned. The table 115 may be motorized so that the vertical and/or lateral position of the table may be adjusted. Accordingly, table 115 may include a motor 116 and a motor controller 118. The table motor controller 118 moves the table 115 by adjusting the motor 116 for appropriately positioning the subject in the gantry 102 for acquiring projection data corresponding to the target volume of the subject. Table motor controller 118 may adjust both the elevation of table 115 (e.g., the vertical position relative to a ground on which the table sits) and lateral position of table 115 (e.g., the horizontal position of the table along an axis parallel to a rotational axis of the gantry).

FIG. 2 illustrates an exemplary imaging system 200 similar to the CT system 100 of FIG. 1. In one embodiment, the system 200 includes the detector array 108 (see FIG. 1). The detector array 108 further includes a plurality of detector elements 202 that together collect the x-ray beams 106 (see FIG. 1) that pass through the subject 112 to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the system 200 is configured to traverse different angular positions around the subject 112 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

In one embodiment, the system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device. While only a single computing device 216 is illustrated in FIG. 2, in some examples computing device 216 may be distributed across multiple physical devices.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the system 200, for example, for inputting or outputting system parameters, requesting examinations, and/or viewing images. Further, in certain embodiments, the system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the system 200 either includes or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

As described further herein, the computing device 216 uses the operator-supplied and/or system-defined commands and parameters to operate the table motor controller 118, which in turn, may control the motorized table 115. For example, the computing device 216 may send commands to the motor controller 118 instructing the motor controller 118 to adjust the vertical and/or lateral position of the table 115 via the motor 116.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the system 200 and instead the computing device 216 may perform one or more functions of the image reconstructor 230. Moreover, the image reconstructor 230 may be located locally or remotely and may be operatively connected to the system 100 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230. In one embodiment, the display 232 allows the operator to evaluate the imaged anatomy. The display 232 may also allow the operator to select a volume of interest (VOI) and/or request patient information, for example, via graphical user interface (GUI) for a subsequent scan or processing.

In some examples, the computing device 216 may include computer-readable instructions executable to send commands and/or control parameters to one or more of the DAS 214, the x-ray controller 210, the gantry motor controller 212, and the table motor controller 226 according to an exam imaging protocol that includes clinical task/intent of the exam. For example, the clinical intent may inform on the goal of the procedure (e.g., general scanning or lesion detection, anatomy of interest, critical to quality (CTQ) parameters, or other goals) based on a clinical indication, and may further define the desired subject position and orientation during the scanning (e.g., supine and feet first). The operator of the system 200 may then position the subject on the table according to subject position and orientation specified by the imaging protocol. Further, the computing device 216 may set and/or adjust various scan parameters (e.g., dose, angle of gantry rotation, kV, mA, attenuation filters) according to the imaging protocol. The imaging protocol may be selected by the operator from among a plurality of imaging protocols stored in memory on the computing device 216 and/or a remote computing device, or the imaging protocol may be selected automatically by the computing device 216 according to received patient information, for example.

Additionally, in some examples, computing device 216 may include an image sensor data processor 215 that includes instructions for processing imaging information received from an imaging sensor, such as sensor 114 of FIG. 1. The information received from the imaging sensor, which may include depth information and/or visible light information, may be processed to determine various subject parameters, such as subject identity, subject size, current subject position, subject movement, and/or subject emotional state. These subject parameters may be used by the computing device 216 or another suitable device to adjust various parameters of the medical imaging session, such as pausing image acquisition and/or outputting notifications to the subject and/or operator when subject movement is detected, as will be described in more detail below. Further, video stream(s) from the imaging sensor may be displayed via display 232.

The information from the image sensor may be usable by the image sensor data processor 215 to perform tracking of one or more subjects in the field of view of the image sensor. In one example, the image information (e.g., depth information) may be used to perform skeletal tracking, wherein a plurality of joints of the subject are identified and analyzed to determine movement, pose, position, etc., of the subject. The location of the joints during skeletal tracking may be used to determine the subject parameters described above.

FIG. 3 schematically shows an example patient monitoring environment 300 including a medical imaging system 301 and interfacing hardware 315. Medical imaging system 301 is a non-limiting example of CT imaging system 100 and imaging system 200. Medical imaging system 301 includes a CT imager 302 including a gantry 304 that is similar to gantry 102 and thus includes at least one x-ray radiation source configured to project x-rays toward a detector array positioned on the opposite side of the gantry 304. CT imager 302 further includes a table 306, which is similar to table 115 of FIG. 1. CT imager 302 further includes a monitor 308 mounted to a front of gantry 304. Monitor 308 may be positioned so that a patient may view videos, images, notifications, etc., displayed on monitor 308 at one or more stages of an imaging session. For example, if a patient is undergoing an exam that includes a feet-first scanning protocol such that a head of the patient is outside the bore during scanning, the patient may be able to view videos, images, notifications, etc., displayed on monitor 308. CT imager may further include a speaker 316 configured to output audio notifications, music, and/or other audio output to the patient.

Patient monitoring environment 300 includes one or more patient monitoring devices located within and/or around medical imaging system 301. As shown, the one or more patient monitoring devices includes a first image sensor 310 located on the bore of gantry 310. First image sensor 310 is similar to image sensor 114 of FIG. 1, and thus description of image sensor 114 likewise applies to first image sensor 310. The one or more patient monitoring devices may further include a second image sensor 312 located within the bore of gantry 304 and positioned/oriented to image a space under second image sensor 312, such that regions of a patient positioned within the bore may be imaged. Second image sensor 312 may be a visible light (e.g., RGB) camera or an IR camera, similar to image sensor 114 of FIG. 1. By including second image sensor 312 within the bore, regions of the patient within the bore that are not viewable by first image sensor 310 may be imaged. Second image sensor 312 may be coupled to a stationary portion of gantry 304 within the bore.

The one or more patient monitoring devices may further include a microphone 314. As shown, microphone 314 is positioned on gantry 304, though other locations are possible, such as table 306. Microphone 314 may be any suitable microphone that is adapted to capture audio signals. Further, in some examples, the one or more patient monitoring devices may include sensors positioned on or in table 306, on the patient, or other locations. The sensors may include accelerometers or other motion sensors, pressure sensors, etc.

In some examples, the one or more patient monitoring devices may include image sensor(s) positioned in the room housing the CT imager but not on the CT imager itself. For example, as shown in FIG. 3, patient monitoring environment 300 may include a third image sensor 318 and/or a fourth image sensor 320. In the example shown, third image sensor 318 is a wide-angle camera and fourth image sensor 320 is an IR (e.g., depth) camera. However, other configurations are possible, such as a pan zoom tilt (PZT) camera. The third image sensor 318 and/or fourth image sensor 320 may be positioned to image an entirety of the patient being imaged (other than portions of the patient occluded by the gantry 304 when the patient is in the bore) from a top-down view, for example.

In some embodiments, only a subset of the patient monitoring devices described herein may be present within patient monitoring environment 301. In some embodiments, more than one of a given type of patient monitoring device may be present. For example, multiple image sensors may be positioned within the bore, multiple pressure sensors may be positioned on table 306, etc.

As will be described in more detail below, the output from the one or more patient monitoring devices may be used to track a patient state, which may include patient movement and/or a patient emotional state. To track patient movement and/or determine a patient emotional state, the output from the one or more patient monitoring devices may be sent to a suitable computing device, which may process/analyze the patient monitoring data to track patient movement and/or determine a patient emotional state. Further, based on the tracked patient movement and/or determined emotional state, various aspects of an imminent or ongoing medical imaging scanning session (e.g., diagnostic imaging exam) may be adjusted by the computing device and/or in response to a command output by the computing device.

FIG. 3 illustrates example interfacing hardware 315 that may be operably coupled to CT imager 302 and the one or more patient monitoring devices. One or more of the computing devices of the interfacing hardware 315 may be the computing device that receives the patient monitoring data, analyzes the data, and adjusts the parameters of the imaging session in response to the received data, and thus may include instructions stored in non-transitory memory that are executable by a processor to receive the output from the one or more patient monitoring devices, track patient motion and/or determine a patient state based on the output, and adjust one or more parameters of an imaging session based on the patient motion and/or patient state.

The interfacing hardware 315 may be positioned within patient monitoring environment 301 (e.g., in the same room as CT imager 302) and/or the interfacing hardware 315 may be positioned outside of patient monitoring environment 301 (e.g., in an operator room located adjacent to the room housing the CT imager). The interfacing hardware 315 may include an edge device 352, a computing device 354, a cloud-based computing system 356, and a host system comprising a host computing device 358 coupled to a host display device 360. Edge device 352 may be a computing device configured to process data received from CT imager (e.g., projection data received from the detectors of the CT imager) in order to reconstruct one or more images. As such, edge device 352 may be a non-limiting example of image reconstructor 230 of FIG. 2. Computing device 354 may be a non-limiting example of computing device 216, and thus may be configured to send and receive signals to control CT imager 302. Computing device 354 may receive images reconstructed by edge device 352 and/or may reconstruct images based on image data received from CT imager 302. Cloud-based computing system 356 may include one or more servers located remotely from patient monitoring environment 301, and may be configured to store reconstructed images, perform processing intensive tasks (e.g., movement tracking, patient state determination), or perform other tasks. Host computing device 358 may act as an interface between CT imager and the operator of the CT imager, and may be configured to receive input from the operator in order to control various aspects of the CT imager, display relevant information to the operator via the host display device 360, etc.

The various computing devices of the interfacing hardware 315 may communicate with the one or more patient monitoring devices and/or CT imager and one another via a suitable network. The network may comprise one or more interconnected communication networks, including for example, a cellular communication network, a local area network (LAN), a wide area network (WAN), a public network (e.g., the Internet), an enterprise private network, and/or combinations thereof. Network/communication interfaces of the various computing devices disclosed herein may employ one or more suitable communication protocols defining rules and data formats for exchanging information and communicating over the network, such as User Datagram Protocol/Internet Protocol (UDP/IP), and/or Transmission Control Protocol/Internet Protocol (TCP/IP). In some examples, the computing devices, CT imager, and/or one or more patient monitoring devices may connect to the network via a hardwired link, such as an IEEE 802.3 (Ethernet) link, a wireless link using a wireless network protocol, such as an 802.11 (Wi-Fi) link, and/or any other suitable link for interfacing with the network.

In some examples, one or more of the interfacing hardware devices may be combined in one device or may be dispensed with. For example, image reconstruction may be performed by computing device 354, and thus edge device 352 may be dispensed with. Further, in some examples operator communication may be provided via a console of computing device 354, and thus a separate host computing system may be dispensed with. Further, while not shown in FIG. 3, it is to be understood that various other devices may communicate with the devices illustrated in FIG. 3, such as various hospital servers/computing devices (e.g., devices storing/executing a PACS system, electronic medical record database, radiology system, etc.).

FIG. 4 shows a high-level flow chart illustrating an example method 400 for automatic patient monitoring during a medical imaging scanning session. Method 400 will be described with regard to the systems and components of FIGS. 1-3; however, it should be understood that the method may be implemented with other systems and components without departing from the scope of the present disclosure. Method 400 may be carried out according to executable instructions stored in non-transitory memory on a computing device, such as computing device 216 of FIG. 2; computing device 354 of FIG. 3; edge device 352 of FIG. 3; or other computing devices described herein.

AT 402, a selection of an imaging protocol is received. An operator of the medical imaging system may select, via a user interface of the imaging system, an imaging protocol that specifies the anatomy and clinical intent of the exam. The imaging protocol may include information that defines the objective of the scan. For example, the information may comprise an indication of a task (such as detection, screening, and so on), target anatomy being imaged (e.g., abdomen, head, chest, etc.), patient orientation for the exam (e.g., supine or prone, head-first or feet-first), scanning settings (e.g., targeted contrast level, x-ray dose target, temporal resolution, contrast to noise ratio, signal to noise ratio, and low contrast detectability). Further, the imaging protocol may include instructions displayed to the exam operator (such as via display 232 of FIG. 2 or display device 360 of FIG. 3) regarding the exam, such as patient positioning, acceptable levels of motion, whether the patient will be coached through breath holds, etc.

At 404, patient information is received. For example, patient information may be input by the operator or may be obtained from an electronic health/medical record. Patient information may include, but is not limited to, patient age, patient gender, patient size (e.g., height and weight), previous exposure history, and so on. At 406, output from one or more real-time patient monitoring devices is received. The real-time patient monitoring devices may be separate from the imager of the medical imaging system. For example, when the medical imaging system is a CT imaging system, the imager may be a CT machine, while the patient monitoring devices may include visible light and/or IR cameras, accelerometers, pressure sensors, microphones, etc. The data that is output from the patient monitoring devices may be output and processed in real-time as the scanning session proceeds so that a current patient state may be tracked and/or determined. The diagnostic images that are reconstructed from the data obtained the imager of the medical imaging system do not include data output from the one or more patient monitoring devices. For example, the diagnostic images may be CT images reconstructed from projection data output by the CT imager and do not include image information output by the patient monitoring devices. The patient monitoring devices may include first image sensor 310, second image sensor 312, microphone 314, third image sensor 318, fourth image sensor 320, and/or other sensors of FIG. 3 (e.g., movement/motion sensors present in the table or on the patient, such as accelerometers or pressure sensors).

At 408, a diagnostic scan is initiated and performed. The diagnostic scan may be initiated by the scan operator by inputting a start command at the operator console (such as operator console 220 of FIG. 2). During the diagnostic scan, the imaging source (e.g., x-ray projector) is activated according to the parameters specified by the imaging protocol (e.g., at a specified kV, mA, attenuation filter position) and the rotation of the gantry is controlled to achieve the scan angles specified by the imaging protocol. Further, during the scan, the position of the table may be moved such that the scan progresses from the start scan location to the stop scan location.

Initiating and performing the diagnostic scan may include monitoring and/or addressing patient motion before and/or during the diagnostic scan, as indicated at 410. For example, upon the operating inputting the start command, patient motion may be monitored and the diagnostic scan may only be initiated once patient motion has stopped or dropped below a threshold level. Further, during the diagnostic scan, patient motion may be tracked and if patient motion is detected, one or more scanning session parameters may be adjusted, such as pausing scanning, discarding or compensating acquired image data, outputting notifications to the patient and/or operator, etc. Additional details about monitoring patient motion in a medical imaging session are provided below with respect to FIGS. 5A and 5B.

Initiating and performing the diagnostic scan may include monitoring and/or addressing a patient state before and/or during the diagnostic scan, as indicated at 412. For example, the output from the one or more patient monitoring devices may be analyzed to determine a patient emotional state, such as anxiety. If a particular patient state is detected, or if patient state changes during the scanning session, one or more parameters of the scanning session may be adjusted and/or the operator may be notified. Additional details about monitoring patient state in a medical imaging session are provided below with respect to FIG. 6.

At 414, diagnostic image(s) are reconstructed based on data acquired during the scan. The one or more diagnostic images may be reconstructed using, as a non-limiting example, an analytic reconstruction algorithm, such as filtered backprojection or an iterative reconstruction algorithm. At 416, the reconstructed image(s) are output and/or stored. For example, the one or more images may be output to a display device, such as display 232 of FIG. 2. In this way, the operator of the imaging system may review the image(s). Method 400 then ends.

Figure 5A:
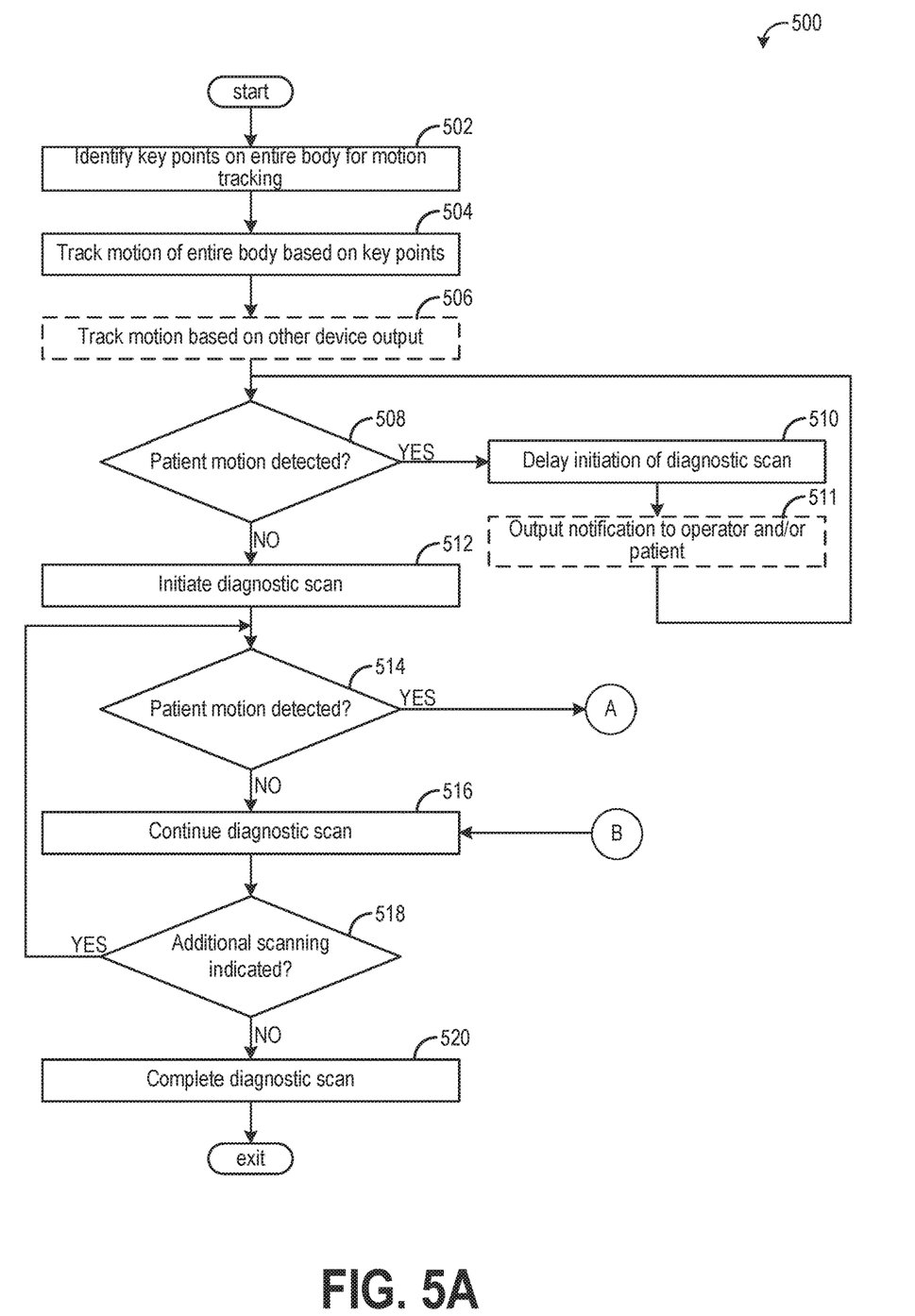
FIGS. 5A and 5B show a flow chart illustrating a method for monitoring and addressing patient movement during a medical imaging session.
Figure 5B:
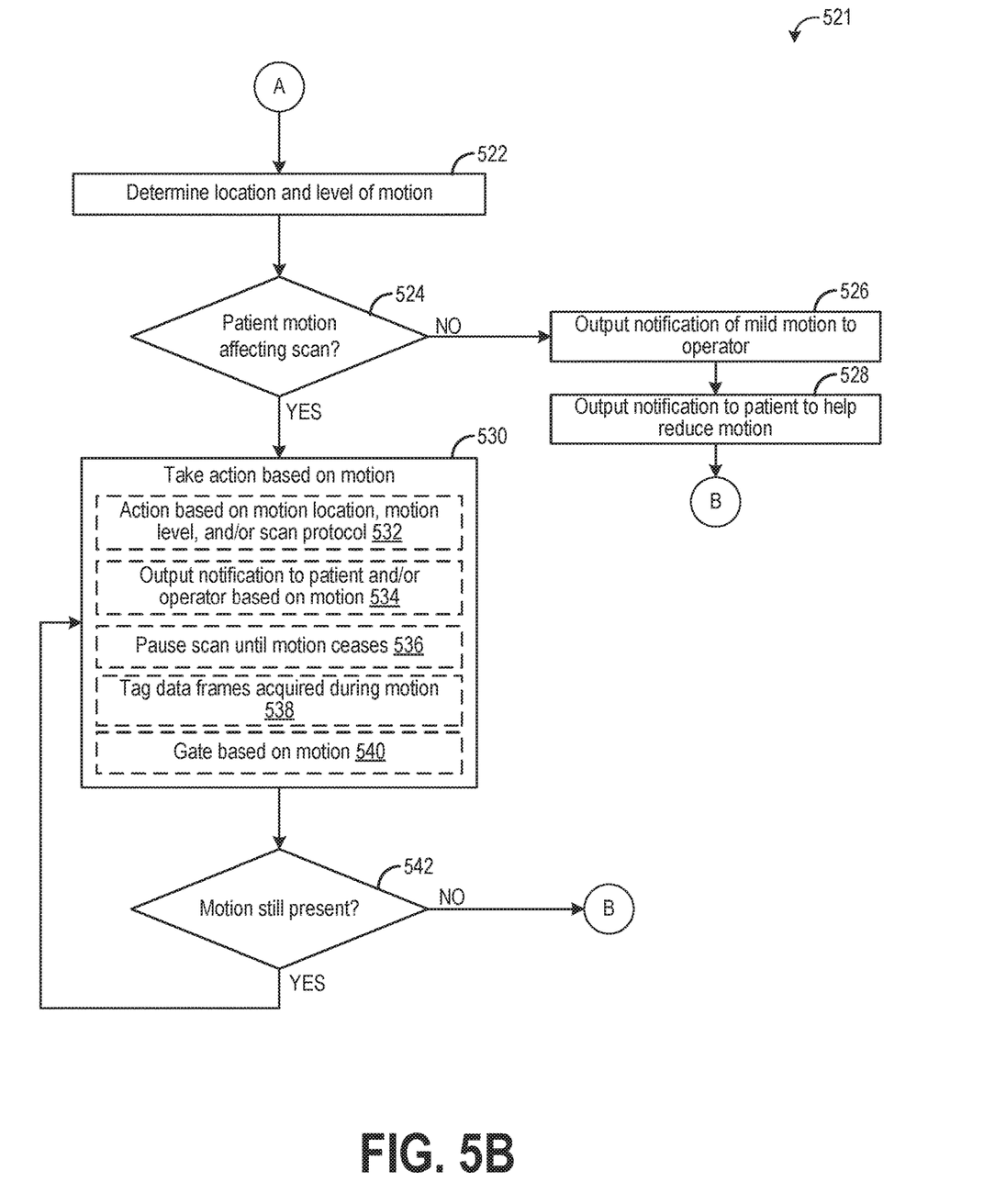

FIGS. 5A and 5B illustrate a method 500 for monitoring patient motion during a medical imaging session. Method 500 may be carried out according to executable instructions stored in non-transitory memory on a computing device, such as computing device 216 of FIG. 2; computing device 354 of FIG. 3; edge device 352 of FIG. 3; or other computing devices described herein. Method 500 may be carried out as part of method 400, e.g., once the diagnostic scan of method 400 is about to commence. Method 500 may be carried out in conjunction with one or more patient monitoring devices (e.g., the patient monitoring devices described above with respect to FIG. 3).

At 502, key points for motion tracking are identified. The key points may be identified for an entire body of the patient undergoing the diagnostic scan. The key points may be identified from the output of one or more image sensors (e.g., first image sensor 310, second image sensor 312, third image sensor 318, and/or fourth image sensor 320). The key points may represent and/or may be located at joints of the patient (e.g., elbows, wrists, ankles, etc.). The key points may be identified once the patient is positioned on the table and before the diagnostic scan has commenced.

At 504, the motion of the entire body of the patient is tracked based on the key points. For example, a skeleton representing the patient may be formed using the key points, and the skeleton may be tracked to determine patient motion. Further, the key point/skeletal tracking may be performed to identify patient pose or other patient parameters. At 506, method 500 optionally includes tracking patient motion based on other patient monitoring device output, such as accelerometer output. In this way, multiple methods may be used to track patient motion, which may improve tracking reliability. In some examples, rather than relying on skeletal tracking, other motion detection methods may be used, such as frame subtraction.

At 508, method 500 includes determining if patient motion is detected. Patient motion may be detected if the skeletal tracking indicates that at least one part of the body of the patient has moved at least a threshold amount. For example, any patient motion above a threshold distance (e.g., 5 mm) and/or rate (e.g., 1 mm per second) may be detected by the skeletal tracking or frame subtraction and identified as patient motion, while smaller amounts/rates of motion may be ignored. In other examples, any detectable patient motion may be identified as patient motion.

If patient motion is detected, method 500 proceeds to 510 to delay initiation of the diagnostic scan. For example, if an operator inputs a start command to initiate scanning (or the system automatically determines that the scan should commence), the output from the one or more patient monitoring devices may be analyzed to track patient motion. If patient motion is detected, the actual start of the diagnostic scan (e.g., activation of the x-ray source and/or sampling of the x-ray detectors) may be delayed until the patient motion subsides. For some patients, the patient motion may be involuntary (e.g., coughing, sneezing) and thus the patient motion may subside without further intervention. In other patients, the patient motion may be voluntary, and thus one or more notifications may be output to the operator and/or patient, as indicated at 511 so that steps may be taken to reduce the motion. For example, an audio notification may output (e.g., via a speaker of the medical imaging system, such as speaker 316) notifying the patient that the diagnostic scan is about to commence and requesting that the patient cease all motion. Further, a visual notification may be output via a display device (e.g., via console 232 or display device 360) to the operator to inform the operator that patient motion is delaying start of the diagnostic scan, which may allow the operator to override the delay or assist the patient in reducing motion. Method 500 then proceeds back to 508 to determine if patient motion is still detected.

If patient motion is not detected, method 500 proceeds to 512 to initiate the diagnostic scan by activating the x-ray source, sampling the x-ray detectors, etc., according to the parameters specified in the scanning protocol. At 514, method 500 again determines if patient motion is detected, which may be determined based on the output of the patient monitoring devices as described above. If patient motion is detected, method 500 proceeds to branch 521 of FIG. 5B, which will be explained in more detail below. If patient motion is not detected, method 500 proceeds to 516 to continue the diagnostic scan. Accordingly, the x-ray source, sampling of the x-ray detectors, gantry rotation, table movement, etc., are all controlled according to the scanning protocol to acquire diagnostic imaging data (e.g., projection data) that will be used to reconstruct the images. At 518, method 500 determines if additional scanning is indicated. For example, additional scanning may be indicated if all target anatomy has not been scanned and/or all specified imaging data has not been acquired (e.g., if the scanning protocol indicates that more scanning is needed to acquire data to reconstruct all the images specified by the scanning protocol). In some examples, the determination of whether or not additional scanning is indicated may be made on the basis of the scanning protocol. In other examples, the determination of whether or not additional scanning is indicated may be made on the basis of operator input, e.g., the system may assume more scanning is indicated unless the operator inputs an end of scan command.

If additional scanning is indicated, method 500 proceeds back to 514 to assess patient motion and, if indicated, continue the diagnostic scan. In this way, patient motion may be tracked and identified during the entire course of the diagnostic scan, such that if motion is detected at any stage of the diagnostic scan, appropriate steps may be taken to address and/or compensate for the motion. If additional scanning is not indicated, for example if all target anatomy has been imaged and data needed to reconstruct all specified images has been acquired, method 500 proceeds to 520 to complete the diagnostic scan. Completing the diagnostic scan may include deactivating the x-ray source, terminating sampling of the x-ray detectors, and/or other actions. As explained above with respect to FIG. 4, diagnostic images may be reconstructed from the image data acquired during the diagnostic scan. Method 500 then ends.

Referring now to branch 521 of method 500 shown in FIG. 5B, in response to determining that patient motion is detected, method 500 proceeds to 522 to determine the location and level of patient motion. The location of the patient motion may be determined relative to the patient's body (e.g., the location may be an anatomical region, such as the fingers or face) and/or relative to the imaging bore or current imaging field of view (e.g., the location may be one or more sets of coordinates defined by the positon of the imaging bore or current imaging field of view of the medical imaging system). In this way, the location of the motion may be assessed relative to where the diagnostic imaging data is actually being acquired. The level of motion may be determined based on a rate of motion, a distance of motion, and/or an extent of motion (such as how much of the patient's body is moving). The level of motion may be represented as graded levels (e.g., low, medium, and high) or as a range of motion values. The location of the motion as well as the level of motion may be used to determine if the motion is affecting the diagnostic scan. For example, if the output from the one or more patient monitoring devices indicates the patient is currently moving, but the location and level of the motion indicates the patient motion is normal breathing patterns and the diagnostic scan is a head scan, the system may determine that the motion is not affecting scanning. However, if the diagnostic scan is a chest scan, the system may determine that the motion is affecting scanning. As another example, if the motion is located at the fingers, but not the arms, shoulders, etc., and the diagnostic scan is a head scan, the system may determine that the motion is not affecting the scan.

Thus, at 524, method 500 determines if the detected patient motion is affecting the diagnostic scan. As mentioned above, the determination of whether the motion is affecting the scan may be based on the location of motion, the level of motion, and the anatomy currently being scanned (the anatomy currently in the field of view of the scanner). Further, whether the motion is affecting the scan may also be determined based on a tolerated level of motion for the scan. For example, some scans may be highly affected by any motion, while other scans may less affected by motion. The tolerated level of motion may be based on the goal of the scan (e.g., lesion monitoring, lesion detection, head trauma detection, etc.), image reconstruction technique, operator preference, etc. If the patient motion is not affecting the scan, method 500 proceeds to 526 to output a notification of mild patient motion to the operator. The notification may be output on a display device viewable by the operator (e.g., console 232 or display device 360). At 528, a notification may be output to the patient to attempt to reduce the motion or prevent escalation of the motion. The notification output to the patient may be an audio notification (e.g., via speaker 316) and/or a visual notification (e.g., via monitor 308), and may include a request to the patient to stop moving or to limit motion. Method 500 then returns back to 516 to continue with the diagnostic scan, although it is to be understood that the diagnostic scan may be ongoing during the motion detection and while the notifications are output.

Returning to 524, if it is determined that patient motion is affecting the scan, method 500 proceeds to 530 to take an action based on the motion. As indicated at 532, taking an action based on the motion may include selecting an action to perform based on the motion location, motion level, and/or scan protocol. For example, if the level of motion is higher, the action taken in response to the motion may be different than if the level of motion is lower. Additionally, the action taken in response to the motion during a first type of scan (e.g., chest scan) may be different than the action taken in response to the motion during a second type of scan (e.g., head scan).

In one example, taking an action based on the motion may include outputting a notification to the patient and/or operator based on the motion, as indicated at 534. The notification(s) may be output via a suitable device or devices (e.g., speaker, display device). One of the notifications may alert the operator to the patient motion, so the operator may instruct/guide the patient not to move or take other suitable action. Further, additionally or alternatively, one of notifications may inform the patient of the motion, identify where the motion is occurring, remind the patient not to move, inform the patient on the outcome/impact of the motion on the scan, and/or update the patient on the status of the scan. For example, a patient may be better able to control his or her motion if the patient knows the exam is nearing completion. In still further examples, the notification output to the patient may coach the patient through a breath hold, depending on the type of scan being performed. Certain types of scans, such as chest scans, may dictate that the patient hold his or her breath during certain phases of the scan to reduce or stop breathing-related motion that can disrupt scanning. If patient motion is detected during or leading up to a breath hold, and the motion is determined to be breathing-related motion (e.g., due to the location of the motion, level of the motion, etc.), the notification may request the patient hold their breath for a given duration.

In another example, taking an action based on the motion may include pausing the diagnostic scan until the motion ceases, as indicated at 536. For example, if the motion is relatively high and in a location where scanning is affected, such that image artifacts may appear due to the motion in the images reconstructed from the data acquired while the motion is occurring, the diagnostic scan may be paused to prevent low-quality data from being acquired. To pause the scan, the computing device may send signals to the x-ray controller, which may in turn control (e.g., deactivate) the radiation source, to the gantry controller, which may in turn halt gantry rotation, and/or to the data acquisition system, which may in turn pause x-ray detector sampling.

In another example, taking an action based on the motion may include tagging data frames acquired by the medical imaging system during the detected motion, as indicated at 538. The tagged data frames may be discarded, if not necessary for the final image reconstruction, or adjusted (e.g., motion compensation may be performed on those frames. In some examples, the tagged data frames may be replaced with new data frames acquired after patient motion ceases.

In another example, taking an action based on the motion may include gating based on the motion, as indicated at 540. Some types of diagnostic scans may dictate that scanning/data acquisition only occur at particular respiratory phases, such as end of expiration, in order to image at times when breathing-related motion is lowest. To achieve this, the operation of the scanner may be gated so that image data is only acquired during the predetermined respiratory phase(s). When motion is tracked as described above, patient breathing cycles may be identified from the motion tracking and used to gate the scanner.

While the actions described above were described individually, it is to be understood that more than one action could be carried out in response to detecting patient motion. For example, a notification may be output to both the operator and the patient, and the scanning may be paused. Further, once motion is detected, the scanning may be paused and all data frames acquired within a predetermined amount of time before the scanning was paused may be tagged as potentially including motion. Other configurations are possible.

At 542, method 500 determines if the motion is still present. If the motion is still present, method 500 returns to 530 to continue to take the action currently be taken (e.g., to continue to pause the scan until the motion stops) and/or take a different action. For example, a notification to the patient may be first be output asking the patient to stop moving, and the motion does not stop, the scan may be paused. If the motion tracking indicates that the patient motion has stopped, method 500 proceeds to 516 to continue with the diagnostic scan, although it is to be understood that the diagnostic scan may be ongoing during some of the actions described herein (e.g., if a notification is output to the patient to stop moving and the patient responds and stops moving, the diagnostic scan may be ongoing while the notification is output and may not be stopped).

Thus, method 500 provides for a system including a camera mounted with a view of the patient table, outside and inside the bore. Using computer vision techniques and data from the depth field of the camera, motion in certain areas of the image may be monitored. This could trigger delay of the start of an exam if the patient is moving, or be used the trigger the start of an exam when the patient becomes still, or pause an exam, or let an exam continue but tag parts of the exam as having motion to either be re-scanned or simply discarded. Especially for uncooperative patients, motion can be hard to control. The method described herein may provide much more data to the tech/operator to indicate when the patient is moving or has moved, and how much motion there was. Currently, the only mechanism available to an operator is to watch through a window into the room housing the imaging system, or to monitor the images as they come back, which is too late to take any action. The method described above allows for images to be acquired with less motion, allows for gating on motion, triggering on motion, and monitoring motion in the scan region of interest.

For example, as explained above, the method may pause or reject data from an exam and respace when involuntary motion from coughing or sneezing occurs, and/or start exam based on lack of motion for pediatric patients or non-compliant patients. The method may apply predictive functions that so patient motion may be predicted based on past detected motion and actions may be taken proactively. Further, in some examples, other biometric data may be incorporated, such as heart rate. The method may monitor motion before and during exams and delay exam start until the patient is still. In some examples, blood flow may be measured near the patient skin surface to perform gating, IR thermal or RGB data may be used. Patient breathing may be monitored with video (RGBD, IRD), assisting with respiratory gating or breath hold checks. As explained above and also in more detail below, visuals for auto breathing and relaxation may be displayed and/or auto detection of a patient falling asleep may be provided, which may allow for the use of haptics or voice to keep the patient awake, or for concussion cases.

Figure 6:
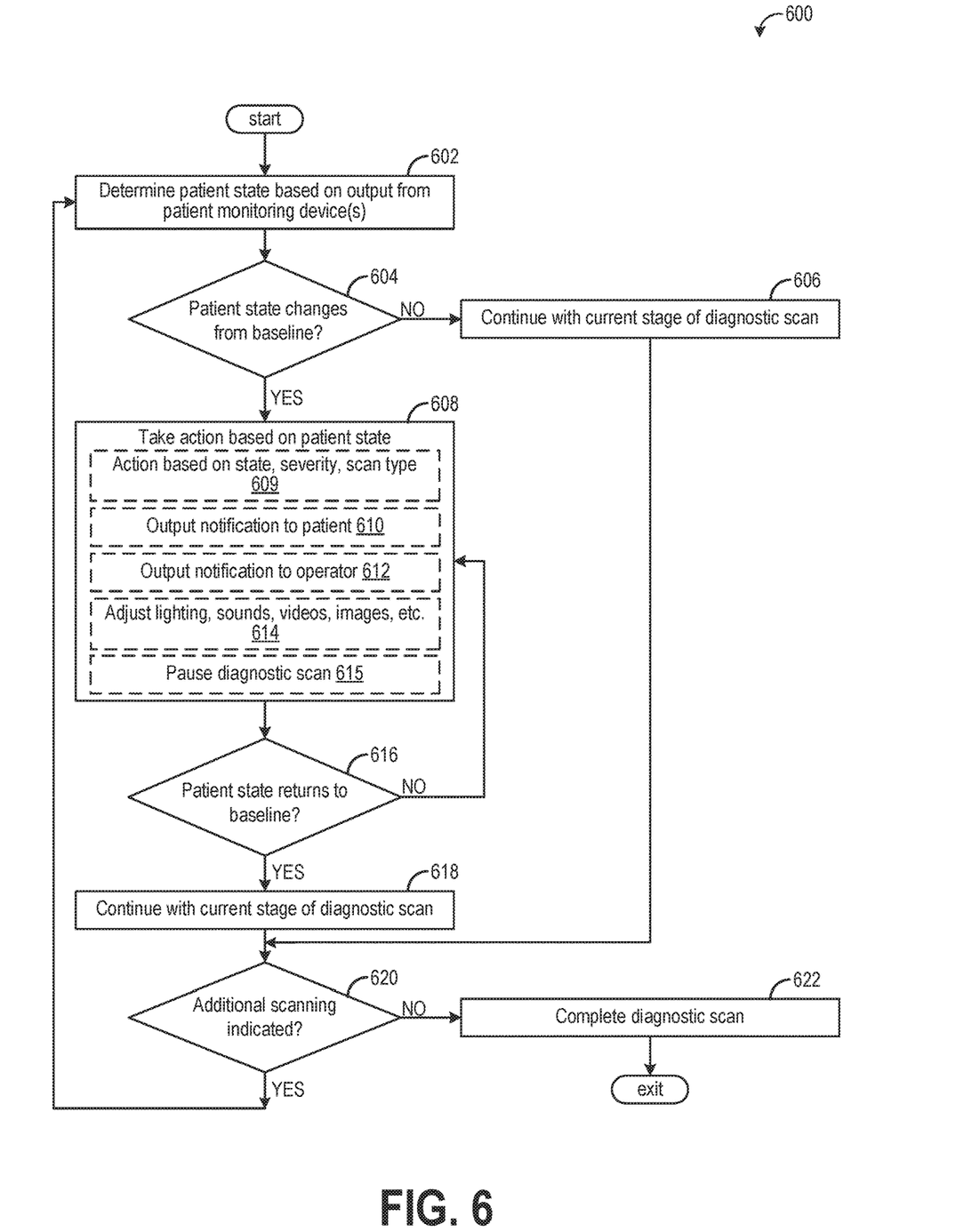
FIG. 6 is a flow chart illustrating a method for monitoring and addressing a patient state during a medical imaging session.
Figure 7:
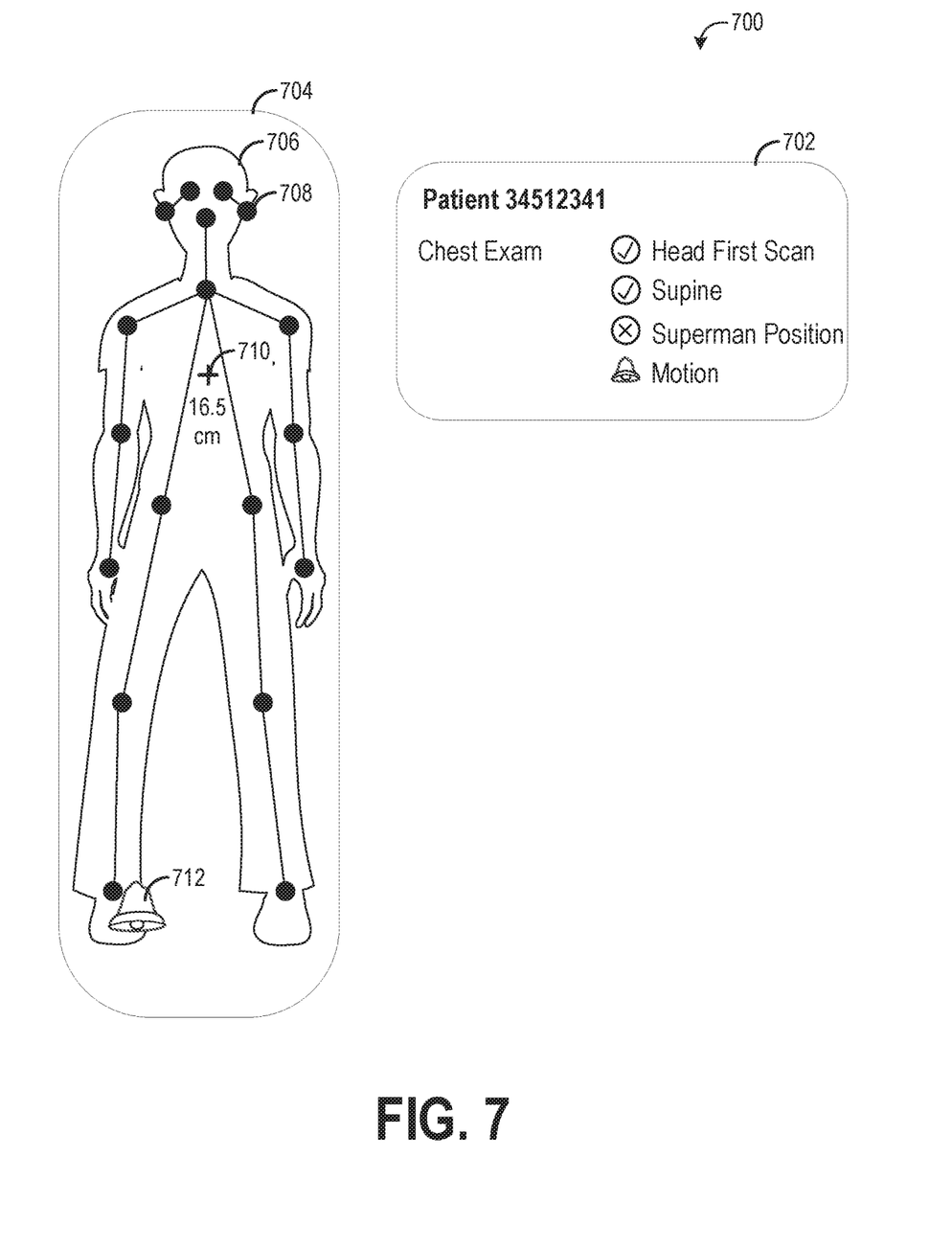
FIG. 7 is an example user interface.

FIG. 6 illustrates a method 600 for monitoring patient state during a medical imaging session. Method 600 may be carried out according to executable instructions stored in non-transitory memory on a computing device, such as computing device 216 of FIG. 2; computing device 354 of FIG. 3; edge device 352 of FIG. 3; or other computing devices described herein. Method 600 may be carried out as part of method 400, e.g., once the diagnostic scan of method 400 is about to commence. Method 600 may be carried out in conjunction with one or more patient monitoring devices (e.g., the patient monitoring devices described above with respect to FIG. 3).

At 602, a patient state is determined based on the output from the one or more patient monitoring devices. The patient state may be an emotional state in some examples, such as anxiety, fear, nervousness, panic, or other emotional state that may pose challenges to a successful diagnostic scan or may induce patient discomfort or dissatisfaction. The patient state may be a physical state in some examples, as such as wakefulness or sleepiness, pose, or other physical state. The patient state may be determined from the patient's facial expressions (as identified from image data collected by the one or more image sensors described above with respect to FIG. 3), breathing rate (which may also be determined by the image data, at least in some examples), patient motion (e.g., finger movement, eye movement), and/or other parameters of the patient that may be detected by the patient monitoring devices (e.g., voice output as captured by a microphone). In some examples, the patient state may be determined when the patient is positioned on the table and before the patient is moved into the bore of the medical imaging system in order to establish a baseline state for the patient, and then patient state may be determined throughout the course of the diagnostic scan.

At 604, method 600 determines if the patient state has changed from the baseline state. For example, the method may determine if the patient has changed from calm to anxious, or from awake to asleep. In some examples, the patient state may change from the baseline to a different that state that does not indicate potential issues with the diagnostic scan, such as if the patient changes from nervous to relaxed as the scan progresses and the patient becomes accustomed to the environment. In such an example, even if the patient state does change, the method may not recognize the change as one that dictates any action. If the patient state has not changed from the baseline, or if the patient state is not associated with any indicated actions, method 600 proceeds to 606 to continue with the current stage of the diagnostic scan and without making any adjustments based on the patient state. Accordingly, the x-ray source, sampling of the x-ray detectors, gantry rotation, table movement, etc., are all controlled according to the scanning protocol to acquire diagnostic imaging data (e.g., projection data) that will be used to reconstruct the images. Method 600 then proceeds to 620 to determine if additional scanning is indicated. For example, additional scanning may be indicated if all target anatomy has not been scanned and/or all specified imaging data has not been acquired (e.g., if the scanning protocol indicates that more scanning is needed to acquire data to reconstruct all the images specified by the scanning protocol). In some examples, the determination of whether or not additional scanning is indicated may be made on the basis of the scanning protocol. In other examples, the determination of whether or not additional scanning is indicated may be made on the basis of operator input, e.g., the system may assume more scanning is indicated unless the operator inputs an end of scan command.

If additional scanning is indicated, method 600 proceeds back to 602 to assess patient state and, if indicated, continue the diagnostic scan. In this way, patient state may be tracked and identified during the entire course of the diagnostic scan, such that if a change in patient state is detected at any stage of the diagnostic scan, appropriate steps may be taken to address the patient state. If additional scanning is not indicated, for example if all target anatomy has been imaged and data needed to reconstruct all specified images has been acquired, method 600 proceeds to 622 to complete the diagnostic scan. Completing the diagnostic scan may include deactivating the x-ray source, terminating sampling of the x-ray detectors, and/or other actions. As explained above with respect to FIG. 4, diagnostic images may be reconstructed from the image data acquired during the diagnostic scan. Method 600 then ends.

Returning to 604, if a change in the patient state is detected, and in particular if the change in patient state is associated with an action to be taken, method 600 proceeds to 608 to take an action based on the patient state. Taking an action based on the patient state may include selecting an action based on the patient state that is identified, the severity of the patient state, and the scan type, as indicated at 609. For example, if the patient is determined to be anxious, a different action may be taken than an action taken if the patient is asleep. Further, if the patient is asleep, a different action may be taken if the scan type is a head scan than an action that may be taken when the scan type is an extremity scan (e.g., it may be desirable to keep the patient awake during a head scan since there is a risk the patient may have a concussion, while patient wakefulness may not matter during a scan of an elbow to look for a fracture).

As an example, taking an action based on patient state may include outputting a notification based on the patient state, as indicated at 610. The notification may be a visual notification, audio notification, and/or haptic feedback. For example, if the patient state indicates that the patient is exhibiting anxiety, fear, panic, or other emotional distress, the notification may include words, instructions, or information intended to calm the patient by keeping the patient informed of the diagnostic scan status, helping control the patient's breathing, or offering reassurances to the patient. In another example, if the patient state indicates the patient is falling asleep during a scan where sleep may not be beneficial (e.g., a head scan), the notification may include a request to refrain from sleeping, haptic feedback, or other output that may increase a level of wakefulness of the patient.

As another example, taking an action based on patient state may include outputting a notification to the operator, as indicated at 612. The operator may be notified of the patient state via a visual notification displayed on a display device, for example. The operator may be notified of the patient state so the operator can assist the patient, pause scanning, or perform other action. As another example, taking an action based on patient state may include adjusting lighting, sounds, videos, images, and so forth that are output to the patient, as indicated at 614. For example, if the patient is displaying signs of distress, soothing lighting, music, and/or images may be output to attempt to calm the patient. In some examples, such as when the patient is a pediatric patient, the room housing the medical imaging system/patient monitoring environment may be made to be part of a theme to engage the patient's attention and minimize patient movement or distress during the diagnostic scan. For example, images may be displayed (e.g., on walls of the room, in the imaging bore, etc.), music may be played, and stories or actions may be described via audio output to recreate a theme, such as an underwater theme, castle/mediaeval theme, an animal theme, etc. If the patient state changes in a manner that indicates the patient may be bored, restless, scared, etc., the lights, music, audio output, etc., may be adjusted in an attempt to re-engage the patient.

As another example, taking an action based on patient state may include pausing the diagnostic scan, as indicated at 615. If the patient state progresses to a point where excess movement may disrupt scanning or the patient is too distressed for scanning to continue, the diagnostic scan may be paused so the patient can be removed, calmed by the operator, or other action. It should be understood that any of the above actions may be performed simultaneously without departing from the scope of this disclosure, or performed in succession.

At 616, method 600 includes determining if the patient state has returned to the baseline state or if the patient state otherwise indicates that the patient is calm enough, sufficiently wakeful, etc., for scanning to continue. If the patient is still exhibit the patient state that previously warranted action, method 600 may return to 608 to continue performing the action or to perform a different action (e.g., if the output notifications were not successful at calming the patient, the diagnostic scan may be paused). If the patient state returned to baseline or the patient is otherwise suitable for scanning to continue, method 600 proceeds to 618 to continue with the current stage of the diagnostic scan (which may include resuming the diagnostic scan if the diagnostic scan were paused).

Thus, method 600 provides for using a camera-based computer vision system to monitor a patient immediately before and during an imaging scan. Patient motion leads to a large number of rejected images. The computer vision system may sense small motions or facial reactions from patients and help to calm them down or comfort them throughout an exam so that they remain still and the exam can be completed. The technologist has many other responsibilities during an exam and is often not able to sense that the patient is starting to move or is worried.

The system may monitor patient motion and facial expressions, and may also link to non-visual biometric data. When the system senses that the patient is becoming anxious, nervous, or frightened, the system may send a flag to the technologist running the exam, and may also auto-generate a voice command encouraging the patient to remain still or calm, or trigger other changes to the system such as lighting or sounds, or projections of images or videos onto the bore, ceiling, or wall. The system may also act with a virtual companion on a display screen or tablet of the patient, telling the patient what is going to happen offering reassurances to the patient, and could possibly follow the patient through the entire workflow (check-in to results being reported). The system may also have awareness of the scan being performed, so that if the patient is wiggling their toes during a head scan, and there is no danger of image quality degradation, no warning would be issued.

Since the technologist is not always able to maintain visual contact with the patient during an exam, or may not be able to see all of the patient, the computer vision system may be able to respond to patient motion much faster and issue audio cues to remain still, remain calm, or indicate that the scan is almost over without distracting or burdening the technologist. The computer vision system may be able to respond faster than a technologist, and the system will always be monitoring while the tech has other responsibilities. If the number of rejected scans is decreased, then there are gains for the hospital in reduced scan time and fewer un-reimbursed exams.

FIG. 7 shows an example user interface 700 that may be displayed on a display device. User interface 700 includes notifications for an operator of a medical imaging system, and thus user interface 700 may be displayed on console 232 or display device 360. User interface 700 includes a patient information box 702 where a patient currently being scanned with the medical imaging system is identified. Further, the patient information box 702 may identify the type of diagnostic scan (e.g., chest exam) and may also provide patient position information, including patient motion, determined based on output from one or more patient monitoring devices (e.g., image sensors). For example, the patient information box 702 may indicate the extent to whether the patient is in the correct position for the current scan (e.g., as shown, the patient is correctly oriented for a head first, supine scan but the patient has not assumed the proper pose for the scan). Further, the patient information box 702 includes a notification that patient motion has been detected.

User interface 700 further includes a patient avatar that shows the patient position relative to the table 704. The avatar is defined by a patient outline 706 and a plurality of key points, such as key point 708. The outline and key points are identified based on the output from the patient monitoring sensors (e.g., the image sensors). The key points correlate to the joints or other articulation points of the patient and are used to model a skeleton for skeleton/key point tracking of the patient motion. In some examples, an entire body of the patient may be tracked, regardless of which portion of the patient is currently being imaged and thus positioned in the bore, as tracking motion of an entire body rather than an individual region of the body may be more accurate. Also shown in the user interface 700 is a maximum depth 710 of the patient and a location of patient motion 712.

It is to be understood that the user interface 700 is exemplary, and other interfaces are possible, with other notifications. Further, in some examples, a key point skeleton of the patient may not be displayed, but rather a predefined outline or other depiction may be displayed, or no depiction of the patient may be displayed.

Thus, the methods and systems provided herein may track patient motion and/or patient state using patient monitoring devices, such as image sensors. The image sensors are distinct from the medical imaging imager and may be used to identify particular actions that should be taken based on the patient motion/state and the type and location of the medical imaging being used for the particular patient. For example, if the left arm of a patient is being scanned, motion of the right arm might be disregarded, but motion of the left arm, shoulder, fingers, etc., may be used to trigger notifications to the operator and special tagging of the medical image data. Further, the notifications to the patient may be specific to when motion in in a particular place is detected. For example, if the left arm is being scanned, the notification to the patient might include "It looks like you are moving your right arm, please try to keep still, especially on your left arm," and the scan may continue. However, if the right arm moves, then a notification is given to the operator that the scan may need to be redone with a message to the patient of "it looks like you moved your left arm. Please try to keep it still while the scan is repeated."

Another example may use different levels of patient communications depending on the level of movement. On a head scan, a low level of movement (e.g., lips moving, eyes moving around nervously) may trigger a first calming notification, but if the head is actually moving side to side then a more stern warning may be output (e.g., "stop moving your head side to side").

A technical effect of detecting patient motion during a diagnostic imaging scan and automatically responding to the motion is more rapid detection and compensation of the motion, which may reduce image artifacts. Another technical effect of detecting patient state during a diagnostic imaging scan and automatically responding to the state is enhanced understanding of patient state, which may improve patient comfort and reduce image artifacts.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising," and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. Although the examples provided herein are related to medical application, the scope of the present disclosure covers non-destructive testing in industrial, biomedical, and other fields. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for a medical imaging system, comprising:
obtaining output from one or more patient monitoring devices configured to monitor a patient before a diagnostic scan executed with the medical imaging system;
receiving a request to initiate the diagnostic scan;
tracking patient motion based on the output from the one or more patient monitoring devices before initiation of the diagnostic scan and while an imaging source is deactivated; and
initiating the diagnostic scan responsive to the tracked patient motion meeting a predetermined condition.

2. The method of claim 1, further comprising, upon initiating the diagnostic scan, tracking patient motion based on the output from the one or more patient monitoring devices, and if the patient motion exceeds a threshold level, taking an action based on the patient motion.

3. The method of claim 2, wherein taking the action based on the patient motion comprises pausing the diagnostic scan until the patient motion reaches or drops below the threshold level.

4. The method of claim 2, wherein taking the action based on the patient motion comprises tagging data acquired by the medical imaging system while the patient motion exceeds the threshold level.

5. The method of claim 4, further comprising, when the patient motion reaches or drops below the threshold level, reacquiring the data that was acquired by the medical imaging system while the patient motion exceeded the threshold level.

6. The method of claim 2, wherein taking the action based on the patient motion comprises outputting a notification to an operator of the medical imaging system and/or the patient.

7. The method of claim 2, wherein taking the action based on the patient motion comprises selecting the action from among a plurality of possible actions based on a location of the patient motion, a diagnostic scan type, and/or a level of the patient motion.

8. The method of claim 7, wherein selecting the action from among the plurality of possible actions based on the location of the patient motion, the diagnostic scan type, and/or the level of the patient motion comprises selecting a first action responsive to the level of the patient motion being below a threshold level and selecting a second action responsive to the level of the patient motion being above the threshold level.

9. The method of claim 8, wherein the first action comprises outputting a notification to the patient requesting the patient stop the patient motion and the second action comprises pausing the diagnostic scan.

10. The method of claim 1, wherein the patient motion meeting the predetermined condition includes the patient motion being below a threshold level, wherein initiating the diagnostic scan includes acquiring medical imaging data of the patient with the medical imaging system, and further comprising responsive to the patient motion being at or above the threshold level, delaying the initiation of the diagnostic scan.

11. The method of claim 1, wherein tracking the patient motion based on the output from the one or more patient monitoring devices comprises tracking the patient motion based on output from one or more image sensors.

12. A method for a medical imaging system, comprising:
obtaining output from one or more patient monitoring devices configured to monitor a patient before and during a diagnostic scan executed with the medical imaging system;
acquiring medical imaging data of the patient with the medical imaging system via activation of an imaging source and sampling of a plurality of detectors;
determining a patient state based on the output from the one or more patient monitoring devices; and
responsive to the patient state meeting a predetermined condition, outputting a notification to the patient and pausing the diagnostic scan;
wherein pausing the diagnostic scan includes deactivating the imaging source and the plurality of detectors.

13. The method of claim 12, wherein determining the patient state comprises determining an emotional state of the patient based on patient motion, wherein the patient state meeting the predetermined condition includes the emotional state including anxiety, nervousness, and/or panic, and further comprising adjusting one or more of lighting, music, videos, and images output to the patient responsive to the patient state meeting the predetermined condition, wherein the patient motion includes a rate of motion and/or a distance of motion.

14. The method of claim 12, wherein determining the patient state comprises determining a level of wakefulness of the patient based on patient motion and/or a patient breathing rate, wherein the patient state meeting the predetermined condition includes the level of wakefulness falling below a threshold level, and wherein outputting the notification to the patient includes outputting haptic feedback and/or outputting a request to refrain from sleeping.

15. The method of claim 12, wherein obtaining the output from one or more patient monitoring devices comprises obtaining the output from one or more image sensors.

16. The method of claim 12, wherein the medical imaging system is a computed tomography imaging system, a positron emission tomography imaging system, a nuclear medicine imaging system, a magnetic resonance imaging system, an x-ray radiography imaging system, an x-ray fluoroscopy imaging system, an interventional imaging system, and/or an ultrasound imaging system.

17. A system, comprising:
a diagnostic medical imager including a bore configured to house a patient being imaged;
one or more image sensors positioned to image the patient when positioned in the bore; and
a computing device configured with executable instructions in non-transitory memory that when executed cause the computing device to:
acquire medical imaging data of the patient with the diagnostic medical imager via activation of an imaging source and sampling of a plurality of detectors;
track patient motion based on output from the one or more image sensors; and
responsive to patient motion exceeding a threshold level, pause the acquisition of the medical imaging data;
wherein pausing the acquisition of the medical imaging data includes deactivating the imaging source and the plurality of detectors.

18. The system of claim 17, wherein the diagnostic medical imager includes an x-ray source that emits a beam of x-rays toward the patient in the bore and a detector that receives the x-rays attenuated by the patient.

19. The system of claim 17, wherein at least one of the one or more image sensors is positioned within the bore.

20. The system of claim 17, wherein the executable instructions are executable to, upon pausing the acquisition of the medical imaging data and responsive to the patient motion falling below the threshold level, resume acquisition of the medical imaging data.

* * * * *